United States Patent
Semba et al.

(10) Patent No.: US 7,214,523 B2
(45) Date of Patent: May 8, 2007

(54) **METHOD FOR PRODUCTION OF S-HYDROXYNITRILE LYASE BY USE OF *ESCHERICHIA COLI***

(75) Inventors: Hisashi Semba, Tsuchiura (JP); Eita Ichige, Kisaradzu (JP); Masaharu Mukouyama, Tsukuba-gun (JP)

(73) Assignee: Nippon Shokubai Co., Ltd., Osaka (JP)

(*) Notice: Subject to any disclaimer, the term of this patent is extended or adjusted under 35 U.S.C. 154(b) by 0 days.

(21) Appl. No.: 10/738,927

(22) Filed: Dec. 16, 2003

(65) Prior Publication Data
US 2005/0032191 A1 Feb. 10, 2005

(30) Foreign Application Priority Data
Dec. 17, 2002 (JP) .............................. 2002-365675

(51) Int. Cl.
C12D 21/06 (2006.01)
C12N 9/88 (2006.01)
C12N 1/20 (2006.01)
C07H 21/02 (2006.01)
A61K 35/78 (2006.01)

(52) U.S. Cl. .................. 435/232; 435/69.1; 435/320.1; 435/252.33; 536/23.2; 530/370

(58) Field of Classification Search ................ 435/232, 435/252.33, 69.1, 320.1; 536/23.2, 23.1; 530/370
See application file for complete search history.

(56) References Cited

U.S. PATENT DOCUMENTS

| | | | |
|---|---|---|---|
| 5,637,503 A | 6/1997 | Brigelius-Flohe' et al. | 435/320.1 |
| 5,885,809 A | 3/1999 | Effenberger et al. | 435/128 |
| 6,046,042 A | 4/2000 | Hasslacher et al. | 435/128 |
| 6,387,659 B1 | 5/2002 | Semba | 435/69.1 |

FOREIGN PATENT DOCUMENTS

| | | |
|---|---|---|
| JP | 11-508775 | 8/1999 |
| JP | 2000-189159 | 7/2000 |
| JP | 2000-189160 | 7/2000 |
| WO | WO 02/10411 A2 | 2/2002 |

OTHER PUBLICATIONS

Hughes et al., "Production and Characterization of a Plant α-Hydroxynitrile Lyase in *Escherichia coli*", Biotechnology and Bioengineering 53:332-336, 1997.
Kim et al., "Inclusion Body Formation of Recombinant β-Galactosidase Fusion Protein in *Escherichia coli*", Korean Biochem. J. 23:281-285, 1990.
Baedeker et al., "Overexpression of a Designed 2.2 kb Gene of Eukaryotic Phenylalanine Ammonia-lyase in *Escherichia coli*", FEBS Letters 457:57-60, 1999.
Hanning et al., "Strategies for Optimizing Heterologous Protein Expression in *Escherichia Coli*", Strategies for Optimizing Heterologous Protein Expression in *Escherichia coli*, Trends in Biotechnology 16:54:-60, 1998.
Humphreys et al., "High-Level Periplasmic Expression in *Escherichia coli* Using a Eukaryotic Signal Peptide: Importance of Codon Usage at the 5' End of the Coding Sequence", Protein Expression and Pruification 20:252-264, 2000.
Makrides, "Strategies for Achieving High-Level Expression of Genes in *Escherichia coli*", Microbiological Reviews 60:512-538, 1996.

*Primary Examiner*—Rebecca E. Prouty
*Assistant Examiner*—Malgorzata A. Walicka
(74) *Attorney, Agent, or Firm*—Fish & Richardson P.C.

(57) ABSTRACT

A method for efficient production of an S-hydroxynitrile lyase by gene recombination using *Escherichia coli* is provided. A gene is formed by altering a codon in an S-hydroxyniitrylase gene originating in cassava (*Manihot esculenta* Crantz) without changing the amino acid sequence thereof till the frequency of codon usage wholly with an amino acid in *Escherichia coli* reaches a level of not less than 5%. According to the method for the production of an S-hydroxynitrile lyase by the use of the gene, the S-hydroxynitrile lyase can be produced in a large amount with an unusually high yield.

7 Claims, 1 Drawing Sheet

SEQUENCE LISTING

<160> NUMBER OF SEQ ID NOS: 6

<210> SEQ ID NO 1
<211> LENGTH: 777
<212> TYPE: DNA
<213> ORGANISM: Manihot esculenta Crantz

<400> SEQUENCE: 1

```
atggtaactg cacattttgt tctgattcat accatttgcc atggtgcatg gatttggcat      60
aagctcaaac cagcccttga gagagctggc cacaaagtca ctgcactgga catggcagcc     120
agcggcattg acccaaggca aattgagcag attaattcat ttgatgaata ctctgaaccc     180
ttattgactt tcttggagaa actccctcaa ggggaaaagg tcatcattgt tggtgagagc     240
tgtgcagggc tgaatattgc tattgctgct gatagatacg ttgacaaaat tgcagctggt     300
```

```
gttttccaca attccttatt gccagacacc gttcatagcc catcttacac tgtggaaaag      360
cttttggagt cgtttcctga ctggagagac acagagtatt ttacgttcac taatatcact      420
ggagagacaa ttacaacaat gaagctgggc ttcgtacttc tgagggaaaa tttatttacc      480
aaatgcactg atggggaata tgaactggca aaaatggtaa tgaggaaggg atcactgttt      540
caaaatgttt tggctcagag accgaagttc accgaaaaag gttacggatc aattaagaaa      600
gtttatattt ggaccgatca agacaaaata tttttaccag actttcaacg ctggcaaatt      660
gcaaactaca aaccagacaa ggtttatcag gttcaaggtg gagatcataa gctccagctt      720
acaaaaactg aggaggtagc tcatattctc caagaggtgg ctgatgcata tgcttga        777

<210> SEQ ID NO 2
<211> LENGTH: 777
<212> TYPE: DNA
<213> ORGANISM: Artificial Sequence
<220> FEATURE:
<223> OTHER INFORMATION: Modified Semba gene

<400> SEQUENCE: 2
atggttactg cacacttcgt tctgattcac accatttgtc acggcgcatg gatttggcac       60
aaactgaaac cggccctgga acgtgctggc acaaagtta ctgcactgga catggcagcc      120
agtggcattg acccgcgtca aattgaacag atcaactctt tcgatgaata ctctgaaccg      180
ctgctgactt tcctggaaaa actgccgcaa ggcgaaaagg ttatcattgt tggtgaaagc      240
tgtgcaggcc tgaacattgc tattgctgct gatcgttacg ttgacaaaat tgcagctggc      300
gttttccaca ctccctgct gccggacacc gttcacagcc cgtcttacac tgttgaaaag      360
ctgctggaat cgttcccgga ctggcgtgac acagaatatt tcacgttcac caacatcact      420
ggcgaaacca tcactaccat gaaactgggt ttcgttctgc tgcgtgaaaa cctgttcacc      480
aaatgcactg atggcgaata tgaactggca aaaatggtta tgcgcaaggg ctctctgttc      540
caaaacgttc tggctcagcg tccgaagttc actgaaaaag gctacggctc tatcaagaaa      600
gtttatattt ggaccgatca agacaaaata ttcctgccgg acttccaacg ctggcaaatt      660
gcaaactaca aaccggacaa ggtttatcag gttcaaggcg gcgatcacaa gctgcagctg      720
acaaaaactg aagaagtagc tcacattctg caagaagttg ctgatgcata cgcttaa        777

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
gggcatatgg ttactgcaca cttcgttctg attcacacc                              39

<210> SEQ ID NO 4
<211> LENGTH: 42
<212> TYPE: DNA
<213> ORGANISM: Artificial Sequence
<220> FEATURE:
<223> OTHER INFORMATION: Primer

<400> SEQUENCE: 4
cccggatcct taagcgtatg catcagcaac ttcttgcaga at                           42

<210> SEQ ID NO 5
<211> LENGTH: 25
```

```
<212> TYPE: DNA
<213> ORGANISM: Artificial Sequence
<220> FEATURE:
<223> OTHER INFORMATION: Primer

<400> SEQUENCE: 5
ccccatatgg taactgcaca ttttg                                         25

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
gggggatcct caagcatatg catcagcc                                      28
```

METHOD FOR PRODUCTION OF S-HYDROXYNITRILE LYASE BY USE OF ESCHERICHIA COLI

BACKGROUND OF THE INVENTION

1. Field of the Invention

This invention relates to a gene containing a DNA coding for S-hydroxynitrile lyase, a recombinant vector plasmid gene possessing the gene, and *Escherichia coli* containing the recombinant vector plasmid gene. This invention further relates to a method for the production of S-hydroxynitrile lyase by the use of recombinant *Escherichia coli* having integrated the gene mentioned above.

2. Description of the Related Art

The S-hydroxynitrile lyase (EC 4.1.2.37) originating in cassava (*Manihot esculenta* Crantz) is an effective enzyme for the synthesis of an optically active S-cyanohydrin from an aromatic or aliphatic carbonyl compound and hydrogen cyanide. The synthesis of the optically active cyanohydrin by the use of this enzyme is very useful for the sake of synthesizing various optically active intermediates. Since this enzyme is contained only in the amount of a mere trace in the tissue of cassava (*Manihot esculenta* Crantz), rose-rubber tree (*Hevea brasiliensis*), etc., however, it has been difficult to utilize this enzyme on a commercial scale.

An example of the production of this enzyme implemented by the culture of recombinant *Escherichia coli* integrating therein a gene coding for S-hydroxynitrile lyase originating in cassava (*Manihot esculenta* Crantz) with a view to solving the problem has been heretofore known (Biotechnol. Bioeng. 53, 332–338, 1997). Since this method obtains an HNL protein by isolating a fusion protein formed in *Escherichia coli* by using a vector having a malE gene and an HNL gene bonded with a polylinker and subsequently severing the fusion protein at the Factor Xa site of the polylinker, this HNL protein turns out to be a recombinant protein having several amino acids added to the N terminal of the inherent S-hydroxynitrile lyase originating in cassava (*Manihot esculenta* Crantz), fails to form the folding of protein successfully, and eventually exhibits a quality different from the inherent quality of the protein. Further, since it has the gene originating in a eucaryote integrated into the *Escherichia coli* which is a procaryote, the recombinant protein consequently obtained has no fully satisfactory specific activity.

An example of the production of the S-hydroxynitrile lyase originating in rose-rubber tree (*Hevea brasiliensis*) effected by similar gene recombination using a yeast (genus *Saceharomyces* or genus *Pichia*), a eukaryotic cell, as a recipient has been known heretofore (official gazette of International Unexamined Patent Publication No. 11-508775). However, this method requires long cultivation time. Also, it is difficult to isolate recombinant proteins from yeast cells whose cell walls are hard to break.

Similarly, an example of the production of the S-hydroxynitrile lyase originating in cassava (*Manihot esculenta* Crantz) effected by the recombination owing to the use of a yeast episome type expression vector, with the yeast (genus *Saccharomyces*-or genus *Pichia*) as a recipient has been known heretofore (official gazette of JP-A-2000-189159 and JP-A-2000-189160). This method similarly suffers from deficiency in specific activity.

In the existing circumstances, the desirability of developing an efficient method for the production of the S-hydroxynitrile lyase by the gene recombination using *Escherichia coli* has come to find growing recognition in consideration of the fact that this method permits easy high density culture and consequently enables the gene and the protein aimed at to be produced in large quantities, the fact that the cell has a thin wall as compared with a yeast and the fracture of this cell allows easy acquisition of a recombinant protein, and the fact that the method for purifying a target gene and protein has been well established.

Even if the amount of the S-hydroxynitrile lyase to be expressed is simply increased, more often than not the bulk of an inactive body of foreign protein, namely the so-called inclusion body, is formed because them is folding of the foreign protein as by the molecular chaperone does not normally function when the foreign protein is produced in a large quantity in the recipient such as *Escherichia coli*. The inclusion body results from the alteration of the three-dimensional structure of a target product and manifests its effect on the intrinsic activity of that target product. The necessity of performing a refolding treatment, therefore, arises. Thus, the desirability of developing a method which does not form such an inclusion body as this has been finding popular recognition.

SUMMARY OF THE INVENTION

The present inventors have succeeded in producing the S-hydroxynitrile lyase in a larger amount than ever by altering a gene coding for the S-hydroxynitrile lyase originating in cassava (*Manihot esculenta* Crantz) so as to permit codon usage having as high frequency of usage in *Escherichia coli* as permissible without changing the sequence of amino acids during the translation of the protein thereby manufacturing a gene possessing a high efficiency of translation in the *Escherichia coli* and integrating this gene in the *Escherichia coli*. They have accomplished this invention as a result. They have further found that, by culturing the *Escherichia coli* at a temperature in the range of 0–35° C., it is made possible to augment the amount of expression and repress the formation of an inclusion body and ensure efficient manufacture of the S-hydroxynitrile lyase. This invention has been perfected as a result.

This invention, by altering the S-hydroxynitrile lyase gene originating in cassava (*Manihot esculenta* Crantz), is enabled to provide a gene which is easily produced in recombinant *Escherichia coli*. Further by the method contemplated by this invention for the production of a S-hydroxynitrile lyase by the use of the gene mentioned above, since the formation of an inclusion body of the recombinant S-hydroxynitrile lyase can be repressed, it is made possible to produce the soluble active type S-hydroxynitrile lyase in a large amount by using the *Escherichia coli* and moreover culture the recombinant *Escherichia coli* at an increased density. Since the culture can be carried out without depletion of the dissolved oxygen during the course of the culture, this invention proves useful also in terms of the efficiency of energy source.

Since the method for the production of the S-hydroxynitrile lyase mentioned above is capable of producing the S-hydroxynitrile lyase in a large amount with very high efficiency, it can be expected to find application to the synthesis of an optically active cyanohydrin and the synthesis of various optically active intermediates.

DETAILED DESCRIPTION OF THE INVENTION

The first aspect of this invention is directed toward a DNA molecule which is formed by altering the codon in an 5-hydroxynitrile lyase originating in cassava (*Manihot esculenta* Crantz) (hereinafter occasionally abbreviated as "SHNL") indicated by the sequence number 1 (referred to as <400> 1 in the SEQUENCE LISTING described below) without changing the amino acid sequence thereof. The resulting codon has a frequency of codon usage of not less than 5% in *Eseherichia coli*.

An amino acid is specified by the combination of three bases called "codons." The number of codons which corresponds to one amino acid is not limited to one. Generally, a plurality of codons exists for one amino acid. For example, Arg corresponds to these six kinds of codons, i.e. CGU, CGC, CGA, CGG, AGA, and AGG and Lys corresponds to only two kinds of codons, i.e. AAA and AAG. It is known that the frequency of codon usage during the translation of a gene varies with species. Generally, the speed of translation is lowered and the amount of expression is decreased as well when a codon having an extremely low frequency of codon usage is present.

SHNL of cassava (*Manihot esculenta* Crantz) uses a codon which conforms to the frequency of codon usage in cassava (*Manihot esculenta* Crantz), a eukaryote. This cassava codon usage frequency differs greatly from that of *Escherichia coli*, a prokaryote. Thus, when the cassava SHNL gene is expressed in *Escherichia coli* by conventional recombination technology, the translation efficiency is low.

The gene of this invention, however, is enabled to increase the amount of the SHNL to be expressed and prevented from changing the amino acid to be coded for by altering the frequency of codon usage wholly with the amino acid in the *Escherichia coli* based on the base sequence of a gene coding for the SHNL indicated by the sequence number 1 (referred to occasionally as "Ori gene") without changing the amino acid sequence. Thus, the protein consequently obtained is perfectly identical in amino acid sequence with the inherent SHNL.

The term "frequency of codon usage" as used in this invention refers to the percentage of the number of usage of one codon relative to the number of usage of codons coding for amino acids of the same species in all the codons contained in all the genes expressed within the *Escherichia coli*.

Here, codons in SEQ ID NO: 1 are replaced by the corresponding *Escherichia coli* codons. Each of the altered codons has a frequency usage of not less than 5%, preferably not less than 7%, in *Escherichia coli*. The reason for setting the lower limit of the frequency at 5% is that using of codons with lower frequencies will possibly prevent the amount of expression from being increased sufficiently. Here, to practice this invention, one can use the distribution data of the frequency of codon usage of *Escherichia Coli* K-12 MG1655 [refer to XanaGenome (Microbial Genome Database)] whose frequency of codon usage has been collected in a database as shown in Table 1 More specifically, Table 1 lists (i) codons for 20 amino acids and stop codons used in *Escherichia Coli* K-12 MG1655, (ii) the usage frequency of each of the amino acids, and (iii) the relative frequency of each codon for a particular amino acid. For example, listed in column 1, row 2 are the six codons for Arg, i.e., CGU, CGC, CGA, CGG, AGA, and AGG; and the respective relative usage frequencies, i.e., 37.89%, 39.79%, 6.43%, 9.80%,3.85%, and 2.23%. The sum of these six relative usage frequencies is 100%. Also listed is the usage frequency of Arg in the *E. coli* strain, i.e., 5.51%. The usage frequencies of all 20 amino acids and the stops codons add up to 100%. The frequency distribution of codon usage indicated in Table 1, however, represents the average obtained of the codons which are possessed by all the genes to be expressed. Since generally scarcely-expressed genes are used in the calculation of this frequency distribution, altering a gene in accordance with the distribution data only might be insufficient for realizing a high expression. To achieve a high expression level, one can select suitable codons having a still larger number of usages in accordance with the number of codon usage of L-aspartase structural gene (shown in Table 2) which is highly expressed in *Escherichia coli*. This table shows the usage of all the codons of the L-aspartase gene and corresponding usage frequencies. The data was obtained by counting the numbers of codon usage in the relevant region of translation based on the base sequence of the L-aspartase gene of the *Escherichia coli* (Nucleic Acids Research, 13 (6), 2063–2074) in conjunction with the corresponding amino acids. The entry titled "TTT-Phe 2 (0.42)" found in Table 2, for example, indicates that "TTT" is a codon for 2 Phe in the L-aspartase gene of *Escherichia coli* and that the two codons correspond to 0.42% of all the codons of the gene. More specifically, the Ori gene-mentioned above, for example, has a codon AGG which codes for Arg and has a frequency of usage of 2.23% according to Table 1. To increase the expression level, one can change this codon to a codon of CGU, which has a frequency of usage of 37.89% and is within the range of not less than 5% mentioned above. To further increase the expression level, one can alter the codon TTT, which codes for Phe and has a frequency of usage of 2 according to table 2 to a codon TTC which has a number of usage of 11. One can alter other codons for adjusting the frequencies of codon usages in the manner mentioned above.

TABLE 1

| *Escherichia coli* K-12 MG1655 | | | | | | | | |
|---|---|---|---|---|---|---|---|---|
| Arg | | | Leu | | | Ser | | |
| CGU ■ | 37.89% | | UUA ■ | 13.10% | | UCU ■ | 14.55% | |
| CGC ■ | 39.79% | | UUG ■ | 12.94% | | UCC ■ | 14.90% | |
| CGA ⏐ | 6.43% | 5.51% | CUU ■ | 10.36% | 10.63% | UCA ■ | 12.36% | 5.81% |
| CGG ■ | 9.80% | | CUC ■ | 10.41% | | UCG ■ | 15.11% | |
| AGA ⏐ | 3.85% | | CUA ⏐ | 3.65% | | AGU ■ | 15.11% | |
| AGG ⏐ | 2.23% | | CUG ■ | 49.53% | | AGC ■ | 27.63% | |

TABLE 1-continued

| Ala | | | Gly | | | Pro | | |
|---|---|---|---|---|---|---|---|---|
| GCU | 16.10% | | GGU | 33.67% | | CCU | 15.86% | |
| GCC | 26.94% | 9.46% | GGC | 40.41% | 7.34% | CCC | 12.41% | 4.42% |
| GCA | 21.31% | | GGA | 10.83% | | CCA | 19.16% | |
| GCG | 35.65% | | GGG | 15.09% | | CCG | 52.58% | |

| Thr | | | Val | | | Ile | | |
|---|---|---|---|---|---|---|---|---|
| ACU | 16.69% | | GUU | 25.84% | | AUU | 50.80% | |
| ACC | 43.41% | 5.38% | GUC | 21.50% | 7.08% | AUC | 41.95% | 5.98% |
| ACA | 13.10% | | GUA | 15.40% | | AUA | 7.26% | |
| ACG | 26.81% | | GUG | 37.26% | | | | |

| Asn | | | Asp | | | Cys | | |
|---|---|---|---|---|---|---|---|---|
| AAU | 45.00% | 3.93% | GAU | 62.82% | 5.12% | UGU | 44.39% | 1.17% |
| AAC | 55.00% | | GAC | 37.18% | | UGC | 55.61% | |

| Gln | | | Glu | | | His | | |
|---|---|---|---|---|---|---|---|---|
| CAA | 34.81% | 4.41% | GAA | 68.90% | 5.72% | CAU | 57.11% | 2.26% |
| CAG | 65.19% | | GAG | 31.10% | | CAC | 42.89% | |

| Lys | | | Phe | | | Tyr | | |
|---|---|---|---|---|---|---|---|---|
| AAA | 76.52% | 4.40% | UUU | 57.38% | 3.88% | UAU | 56.94% | 2.84% |
| AAG | 23.48% | | UUC | 42.62% | | UAC | 43.06% | |

| Met | | | Trp | | | Stop | | |
|---|---|---|---|---|---|---|---|---|
| AUG | 100.00% | 2.79% | UGG | 100.00% | 1.52% | UAA | 62.74% | 0.33% |
| | | | | | | UAG | 7.88% | |
| | | | | | | UGA | 29.38% | |

TABLE 2

Frequency of codon usage in L-aspartase structural gene

| codon | amino acid | Number of usage | Frequency of usage | codon | Amino acid | Number of usage | Frequency of usage |
|---|---|---|---|---|---|---|---|
| TTT | Phe | 2 | 0.42 | TCT | Ser | 8 | 1.67 |
| TTC | Phe | 11 | 2.3 | TCC | Ser | 6 | 1.25 |
| TTA | Leu | 0 | 0 | TCA | Ser | 1 | 0.21 |
| TTG | Leu | 4 | 0.84 | TCG | Ser | 0 | 0 |
| CTT | Leu | 2 | 0.42 | CCT | Pro | 2 | 0.42 |
| CTC | Leu | 2 | 0.42 | CCC | Pro | 0 | 0 |
| CTA | Leu | 0 | 0 | CCA | Pro | 4 | 0.84 |
| CTG | Leu | 36 | 7.52 | CCG | Pro | 13 | 2.71 |
| ATT | Ile | 11 | 2.3 | ACT | Thr | 10 | 2.09 |
| ATC | Ile | 21 | 4.38 | ACC | Thr | 12 | 2.51 |
| ATA | Ile | 0 | 0 | ACA | Thr | 1 | 0.21 |
| ATG | Met | 16 | 3.34 | ACG | Thr | 1 | 0.21 |
| GTT | Val | 18 | 3.76 | GCT | Ala | 14 | 2.92 |
| GTC | Val | 7 | 1.46 | GCC | Ala | 8 | 1.67 |
| GTA | Val | 11 | 2.3 | GCA | Ala | 13 | 2.71 |

TABLE 2-continued

Frequency of codon usage in L-aspartase structural gene

| codon | amino acid | Number of usage | Frequency of usage | codon | Amino acid | Number of usage | Frequency of usage |
|---|---|---|---|---|---|---|---|
| GTG | Val | 7 | 1.46 | GCG | Ala | 7 | 1.46 |
| TAT | Tyr | 5 | 1.04 | TGT | Cys | 4 | 0.84 |
| TAC | Tyr | 11 | 2.3 | TGC | Cys | 7 | 1.46 |
| TAA | *** | 1 | 0.21 | TGA | *** | 0 | 0 |
| TAG | *** | 0 | 0 | TGG | Trp | 0 | 0 |
| CAT | His | 1 | 0.21 | CGT | Arg | 8 | 1.67 |
| CAC | His | 7 | 1.46 | CGC | Arg | 6 | 1.25 |
| CAA | Gln | 3 | 0.63 | CGA | Arg | 0 | 0 |
| CAG | Gln | 16 | 3.34 | CGG | Arg | 0 | 0 |
| AAT | Asn | 3 | 0.63 | AGT | Ser | 3 | 0.63 |
| AAC | Asn | 33 | 6.89 | AGC | Ser | 3 | 0.63 |
| AAA | Lys | 24 | 5.01 | AGA | Arg | 1 | 0.21 |
| AAG | Lys | 3 | 0.63 | AGG | Arg | 1 | 0.21 |
| GAT | Asp | 8 | 1.67 | GGT | Gly | 21 | 4.83 |
| GAC | Asp | 11 | 2.3 | GGC | Gly | 12 | 2.51 |
| GAA | Glu | 34 | 7.1 | GGA | Gly | 1 | 0.21 |
| GAG | Glu | 4 | 0.84 | GGG | Gly | 0 | 0 |

*** shows termination codons in the table.
Frequency of codon usage were calculated by (number of uses of a codon/the number of all of the codons in L-aspartase) × 100

Generally, when a recombinant protein is produced, the cells are adversely affected as by the toxicity thereof and, as a result, the final cell density is lowered. The present inventors have found that when the gene of this invention is expressed by a culture carried out under the condition of a low temperature, the cell density higher than that which is obtained by the nonrecombinant strain which is incapable of producing a recombinant protein can be attained.

The most preferred mode of this invention consists in the DNA which is indicated by the (SEQ ID NO:2). This gene excels in the yield of the active type SHNL.

The second aspect of this invention is directed toward a recombinant vector plasmid gene which contains the gene of this invention described above.

In this invention, the recombinant vector plasmid gene can be prepared by joining the gene of this invention described above into an expression vector which has been digested with a proper restriction enzyme.

As concrete examples of the mode of the recombinant vector plasmid gene in this invention, plasmid, cosmid, artificial chromosome, and phage may be cited. Further, the recombinant vector plasmid gene contemplated by this invention may contain at least one such selective marker as is capable of selecting the Escherichia coli which has been transformed by the gene of this invention. As concrete examples of the selective marker of this kind, such antibiotic substances as kanamycin, ampicillin, tetracycline, and chloramphenicol may be cited, though not exclusively.

In this invention, the recombinant vector is preferred to have resulted from connecting to the gene of this invention a promoter inductive of the expression of the gene of this invention or other control sequence such as, for example, the ribosome binding site for the expression of a microorganism, the polyadenylating signal, the transfer terminating sequence, the upstream control region, the enhancer, the operator, and the signal sequence. The promoter or other control sequence of this nature does not need to be particularly restricted but may be arbitrarily selected from among those already known in the field. As concrete examples, T7 promoter, Lac promoter, and Tac promoter may be cited. The recombinant vector may contain an adjusting sequence which is capable of adjusting the expression of a protein in addition to the control sequence mentioned above.

A more preferred mode of this invention consists in using the vector pET and the vector pKK223-3, most favorably the vector pET, as the recombinant vector containing the gene of this invention. This choice of the vector has resulted from the search for a vector possessing a more potent promoter because the effect of the gene of this invention resides in exalting the speed of translation of a recombinant protein and, consequently, the gene of this invention can no longer be expected to bring the effect of enhancing the productivity when the speed of transfer from DNA to mRNA reaches the rate determining step.

For the preparation of a plasmid having inserted therein the SHNL gene, any of the methods well known in the art may be adopted. The gene of this invention, for example, can be synthesized by a popularly known method. For the purpose of insertion into a vector, it may be amplified by the PCR method using a primer so as to contain restriction sites of a proper restriction enzyme at the opposite terminals thereof. The conditions of the PCR reaction can be properly decided by any person of ordinary skill in the art. The amplified gene, for example, can be obtained by performing a total of 30 cycles, each consisting of a denaturation at 98° C. for 30 seconds, an annealing at 57° C. for 15 seconds, and a polymerization at 74° C. for 30 seconds.

For the purpose of inserting the DNA fragment containing the gene of this invention into a recombinant vector, the action of a proper restriction enzyme on the vector mentioned above suffices. The restriction enzyme does not need to be particularly discriminated but is only required to be capable of giving rise to a terminal which can undergo ligation with the DNA fragment to be inserted. The reaction conditions for the digestion with the restriction enzyme such as the reaction temperature and the reaction time can be set properly to suit the enzyme to be selected. The vector, when necessary, may be refined by such refining means as the boiling method and the alkali SDS method and may be further concentrated by such means as the ethanol precipitation method and the polyethylene glycol precipitation method, for example.

In the process of treatments mentioned above, the combination of restriction enzymes for digesting the inserted DNA fragment and the vector may be properly selected from among the combinations which are well known in themselves in the present technical field.

Subsequently, by mixing the amplified gene of this invention and the vector mentioned above and then causing a ligase such as, for example, the T4DNA ligase or the DNA ligase originating in *Escherichia coli* to react on the resultant mixture, it is made possible to obtain the recombinant vector plasmid gene. Preferably, the recombinant vector plasmid gene can be obtained by performing a reaction of ligation under prescribed conditions using a commercially available ligation kit such as, for example, Ligation high (made by Toyobo K.K.).

Then, for the purpose of inducing expression of the gene of this invention, a competent cell is transformed by using the recombinant vector plasmid gene containing the acquired gene. The competent cell that fits this invention does not need to be particularly restricted but is only required to be a strain which is incapable of expressing a protein by the pET system and which has a high efficiency of transformation. For example, the *Escherichia coli* DH 5α competent cell can be used. The *Escherichia coli* DH 5α can be advantageously used in this invention because it permits strain organization without fearing toxicity and exhibits a high efficiency in effecting transformation as well. For the transformation of a competent cell with a recombinant vector plasmid gene containing the gene of this invention, the chemical competent cell method and the electroporation method which are in popular use can be adopted.

The *Escherichia coli* transformed by the gene of this invention can be selected by forming a colony on an LB culture agar plate containing such an antibiotic substance as ampicillin or kanamycin, for example, with the marker gene which is possessed by the vector plasmid gene thereof. For the purpose of confirming whether or not the *Escherichia coli* cloned has been transformed by the gene of this invention, part of this *Escherichia coli* may be subjected to confirmation of amplification of an insert by the PCR method or to analysis of sequence by the dideoxy method using a sequencer.

The *Escherichia coli* transformed with the gene of this method which is obtained by the method described above can be cultured in a proper culture medium to produce a recombinant vector plasmid gene in a large amount. For this culture, the LB liquid culture medium and M9 culture medium which are in popular use may be adopted. The recombinant vector plasmid gene can be recovered by using any of the well-known methods. Preferably, the recombinant vector plasmid gene can be obtained under specific conditions using a plasmid recovery kit such as, for example, QIAprep (registered trademark designation) Spin Mini prep kit (made by QIAGEN Corp.). The third aspect of this invention is directed toward *Escherichia coli* which contains the recombinant vector plasmid gene of this invention described above.

The *Escherichia coli* in this invention is prepared by transforming *Escherichia coli* with the recombinant vector plasmid gene of this invention. The *Escherichia coli* thus used does not need to be particularly restricted but is only required to be transformed with a vector plasmid gene which contains the gene of this invention and to be capable of inducing expression of the gene of this invention.

A more preferred mode of this invention resides in using the BL21 (DE3) cell, the BL21plusS cell, the OrigamiB2 cell, and most advantageously the BL21 (DE3) cell in terms of the excellence of productivity, for example, as the *Escherichia coli* containing the recombinant vector plasmid gene of this invention.

The fourth aspect of this invention is directed toward a method for the production of S-hydroxynitrile lyase, characterized by culturing the *Escherichia coli* integrating the gene of this invention at a lower temperature in the range of 0–35° C. than the temperature, 37° C., which is generally used for the culture of *Escherichia coli*.

In this invention, by introducing the recombinant vector plasmid gene containing the gene of this invention into *Escherichia coli* by transformation and culturing this *Escherichia coli* at a temperature in the range of 0–35° C., it is made possible to produce an active type SHNL in a satisfactory yield with high efficiency.

As regards the mode of culture of the *Escherichia coli* which is a transformed body, the conditions of this culture may be selected in due consideration of the nutritional physiological properties of the *Escherichia coli*. In most cases, this culture may be carried out in the form of solution culture. It is advantageous to carry out the culture on a commercial scale in the form of aerated stirred culture using a jar fermenter, for example.

As the source of nutrient for the culture medium, a wide variety of sources of nutrients which are in popular use for the culture of *Escherichia coli* are available. The source of carbon is only required to be an assimilable carbon compound. As concrete examples of the source of carbon which can be used, polyols such as glycerin and such organic acids as pyruvic acid, succinic acid, and citric acid may be cited. The source of nitrogen is only required to be a utilizable nitrogen compound. As concrete examples of the source of nitrogen, peptone, meat extract, yeast extract, casein hydrolyzate, alkali extract of soybean curd, and ammonia and salts thereof maybe cited. Besides, phosphates, carbonates, sulfates, and salts of magnesium, calcium, potassium, iron, manganese, and zinc, specific amino acids, specific vitamins, and defoaming agent may be used as occasion demands. Such protein expression inducing agents as isopropyl-β-D-thiogalactopyranoside, when necessary, may be added to the culture medium.

Though the cultivation temperature may be properly changed within the range in which the *Escherichia coli* is grown and the SHNL is produced, this invention uses it preferably in the range of 0–35° C., more preferably in the range of 10–27° C., and particularly preferably in the range of 10–19° C. If this temperature exceeds 35° C., the excess will render efficient production of the SHNL difficult because it adds to the inclusion body, namely the inactive type SHNL. Conversely, if the temperature falls short of 0° C., the shortage will result in decreasing the total amount of the SHNL to be produced because it markedly lowers the speed of the growth of *Escherichia coli*. This invention contemplates the culture at such a low temperature as falls in the range of 0–35° C. because it is thought to repress the growth of *Escherichia coli*, lower the speed of translation of the SHNL, secure time enough for the SHNL to form its inherent three-dimensional structure, consequently repress the formation of the inclusion body of inactive SHNL, and allow a soluble active SHNL to be efficiently obtained. Further, by the low-temperature culture, it is made possible not only to heighten relatively the concentration of saturated dissolved oxygen in the culture broth but also to lower the speed of consumption of oxygen due to the repressed speed of the growth of *Escherichia coli*, prevent the concentration of dissolved oxygen from being suddenly lowered, and enable an aerobic environment of a high energy efficiency to be maintained. That is, the dissolved oxygen concentration in the culture broth may be properly changed to suit the nature of the recipient to be used as an expression system. When *Escherichia coli* is used as the recipient as in the case of this invention, it is made possible by maintaining the dissolved oxygen concentration in the culture broth in excess of 0 ppm to exalt the efficiency of energy and enable the SHNL to be produced in a large amount with a small source of nutrient. This invention is enabled by the low-temperature culture to repress sudden growth of the *Escherichia coli* and maintain the aerobic environment as well, enhance the efficiency of the utilization of the source of nutrient, and allow the SHNL to be produced in a high yield.

The cultivation time varies more or less with the cultivation conditions. Generally, the SHNL activity assumes the highest magnitude after the growth of cells has entered the stationary phase and rapidly decreases thereafter. It is, therefore, most favorable to recover the cells at the time that the growth of cells has reached the stationary state. Generally, the cultivation time is in the approximate range of 48–66 hours. The pH value of the culture medium may be properly changed within the range in which the growth is continued safely and the produced SHNL is enabled to keep the activity thereof intact. It is preferably in the approximate range of pH 4–8.

As regards the method for recovering the SHNL which has formed in the culture, the cells in accordance with an ordinary method are collected from the produced cell by such means as filtration or centrifugal separation, then broken by a mechanical method, an enzymatic method using lysozyme, or a chemical treatment using a surfactant, for example, and, as occasion demands, further caused to have the SHNL solubilized by the addition of a chelating agent such as EDTA or a surfactant, with the result that the SHNL is separated and collected in the form of an aqueous solution.

For the purpose of further refining the SHNL from the crude enzyme solution mentioned above, the ordinary method for refining a protein may be adopted. To be specific, the method of ammonium sulfate fractionation, the method of organic solvent precipitation, the method of adsorptive treatment using an ion exchanger, the ion-exchange chromatography, the hydrophobic chromatography, the gel filtration chromatography, the affinity chromatography, and the method of electrophoresis may be used either singly or as properly combined.

EXAMPLES

Now, this invention will be described below with reference to working examples. It should be noted, however, that this invention is not limited to the following examples.

Example 1

For the purpose of inserting the gene of this invention indicated by the (SEQ ID NO:2) (hereinafter referred to occasionally as "Semba gene") into a recombinant vector, a PCR primer (Sense: GGG CAT ATG GTT ACT GCA CAC TTC GTT CTG ATT CAC ACC (SEQ ID NO:3); Antisense: CCC GGA TCC TTA AGC GTA TGC ATC AGC AAC TTC TTG CAG AAT (SEQ ID NO:4)) was synthesized and subjected to a PCR reaction with the Semba gene as a template. The gene used as the template here was manufactured by dividing the Semba gene into several oligomers, entrusting Espec Origo Service K.K. to form genes respectively for the oligomers, and connecting the origomers by the PCR method. The primers mentioned above had the restriction sites of restriction enzymes NdeI and BamHI contained in advance therein. By using the restriction enzymes NdeI and BamHI, it was made possible to connect the Semba gene and the recombinant vector.

The PCR reaction performed in this case consisted of one cycle of incubation at 98° C. for five minutes, 30 cycles of incubation (each using 98° C. for 30 seconds, 57° C. for 15 seconds, and 74° C. for 30 seconds), and a final cycle of incubation at 4° C. for a period in the range of 5 minutes–one hour.

When the PCR product mentioned above was assayed by the commonly known method of electrophoresis, it was confirmed to contain genes corresponding to the Semba gene.

For the purpose of inducing the expression of the Semba gene mentioned above to be expressed in *Escherichia coli*, the pET21a vector possessing a T7 promoter having a potent gene expressing ability (made by Novagen Corp.) was subjected to subcloning. The method adopted for the subcloning comprised treating the pET21a vector and the Semba gene with restriction enzymes NdeI and BamHI and subjecting them to ligation by a specified method using a Ligation high Kit (made by Toyobo K.K.).

The *Escherichia coli* DH5α competent cell was transformed by using a pET21a mixed solution which had a Semba gene incorporated therein and had been obtained as described above. Thereafter, the product of this transformation was spread on an LB agar culture medium and incubated thereon at 37° C. for 12–16 hours.

From the colonies of the transformed *Escherichia coli* grown on the LB agar culture medium mentioned above, 10 colonies were selected arbitrarily and subjected to identification of colony by the colony PCR method.

The colonies which had been confirmed to have admitted an insert were severally cultured in an LB liquid culture medium at 37° C. for eight hours. From each of the formed cultures, a plasmid was recovered in the same manner as described above. The plasmids were designated as pET21a/Semba.

*Escherichia coli* strain BL21 (DE3) (made by Novagen Corp.) was transformed by using the pET21a/Semba thus obtained The gene recombinant *Escherichia coli* thus obtained was designated as BL21/pET21a/Semba.

The recombinant *Escherichia coli* strain (BL21/pET21a/Semba) organized as described above was cultured by the following method to obtain a recombinant protein. First, the portion of the strain equivalent to one colony was inoculated to 5 mL of an LB culture medium in a 15-mL test tube and precultured at a temperature of 37° C., at a shaking rate of 170 rpm, for 12 hours. Subsequently, in a 500-mL Sakaguchi flask, each preculture broth 2 mL in volume was inoculated to 100 mL of an LB culture medium, isopropyl-β-D-thiogalacto-pyranoside (IPTG), a protein expression inducing agent, was added thereto till the final concentration thereof reached 1 mM, and they were subjected to regular culture at a temperature of 37° C. at a agitation rate of 130 rpm for 12 hours.

After the culture mentioned above, The final cell concentration of culture broth was measured by determining the absorbance of the broth at 660 nm. During the course of the culture mentioned above, the culture broth was sampled at intervals of six hours. The cell pellet was collected by centrifugation of the culture broth and homogenized. Then the homogenate was divided into a soluble supernatant and an insoluble precipitate fraction.

SHNL activity of the soluble supernatant obtained as measured by the method of a patent publication (JP-A-2000-189160).

Comparative Example 1

The Ori gene indicated by the sequence number 1 was prepared in accordance with Literature (Arch. Biochem. Biophys. 311, 496–502, 1994).

Then, the Ori gene was subjected to cloning by the method of the patent publication (JP-A-2000-189160).

The Ori gene, by the use of a PCR primer (Sense: CCC CAT ATG GTA ACT GCA CAT TTT G (SEQ ID NO:5); Antisense: GGG GGA TCC TCA AGC ATA TGC ATC AGC C (SEQ ID NO:6)), was subjected to organization of gene recombinant Escherichia coli strain, culture, determination of final cell density, and determination of activity of SITTNL by following the procedure of Example 1. Though the restriction enzyme used herein was different from that used in the working example, this difference brought no effect on the quality of the promoter activity of the expression vector pET21 a. The recombinant *Eschenichia coli* obtained here was designated as BL21/pET21 a/Original.

Separately, a BL21 (DE3) incorporating therein a pET21a vector containing no insert was prepared. This was designated as BL21/pET21a/Control. The cells were cultured under the same conditions as in Example 1 and then final cell density and activity were measured. These results are shown in Table 3.

TABLE 3

| Strain | Final cell density (0D660) | Magnitude of activity (U/mL-broth) | Magnitude of specific activity (U/mg-protein) |
|---|---|---|---|
| BL21/pET21a/Control | 2.49 | nd | nd |
| BL21/pET21a/Original | 2.97 | 0.092 | 0.24 |
| BL21/pET21a/Semba | 3.27 | 0.232 | 0.62 |

Example 2

The gene recombinant *Escherichia coli* BL21/pET21a/Semba organized in Example 1 was further subjected to a low-temperature culture (27° C., 22° C., 19° C., 17° C.) by the following method.

First, in a 15-mL test tube, the portion of the strain equivalent to one colony was inoculated to 5 mL of an LB culture medium and precultured at a temperature of 37° C. at a agitation rate of 170 rpm for 12 hours. Subsequently, in a 500-mL Sakaguchi flask, the preculture broth 2 mL in volume was inoculated to 100 mL of a nutritive culture medium (composition of culture medium: 40 g of glycerol, 10 g of ammonium sulfate (($NH_4$)$_2$$SO_4$), 2 g of potassium dihydrogen phosphate ($KH_2PO_4$), 6 g of dipotassium hydrogen phosphate ($K_2HPO_4$), 40 g of yeast extract, 1 g of magnesium sulfate ($MgSO_4$), 20 drops of Adekanol in 1 L of distilled water, pH 6), isopropyl-β-D-thiogalactopyranoside (IPTG), a protein expression inducing agent, was added thereto till the final concentration thereof reached 1 mM, and they were subjected to regular culture at a agitation rate of 130 rpm at temperatures of 27° C., 22° C., 19° C., and 17° C. till the culture reached the stationary state.

After the culture mentioned above, The final cell density of the produced culture broth was measured by following the procedure of Example 1. During the course of the culture mentioned above, the culture broth was sampled at intervals of six hours. The cell pellet was collected by centrifugation of the culture broth and homogenized. Then the homogenate was divided into a soluble supernatant and an insoluble precipitate fraction.

The activity of SHNL of the soluble supernatant obtained here was measured by the same method as in Example 1. The results are shown in Table 4.

Comparative Example 2

Culture, measuring of final cell density and activity of SHNL were carried out on the same gene recombinant *Escherichia coli* BL31/pET21a/Semba as used in Example 2 while using a cultivation temperature of 37° C. The results are shown in Table 4.

TABLE 4

| Strain | Final cell density (0D660) | Magnitude of activity (U/L-broth) | Magnitude of specific activity (U/mg-protein) |
|---|---|---|---|
| BL21/pET21a/Semba 37° C. | 10.6 | 230 | 0.17 |
| BL21/pET21a/Semba 27° C. | 38.08 | 11140 | 5 |
| BL21/pET21a/Semba 22° C. | 27.88 | 34658 | 10.33 |
| BL21/pET21a/Semba 19° C. | 37.12 | 79180 | 13.52 |
| BL21/pET21a/Semba 17° C. | 51.12 | 215600 | 29.08 |
| BL21/pET21a/Original 17° C. | 20.42 | 784 | 0.65 |

Figure 1:
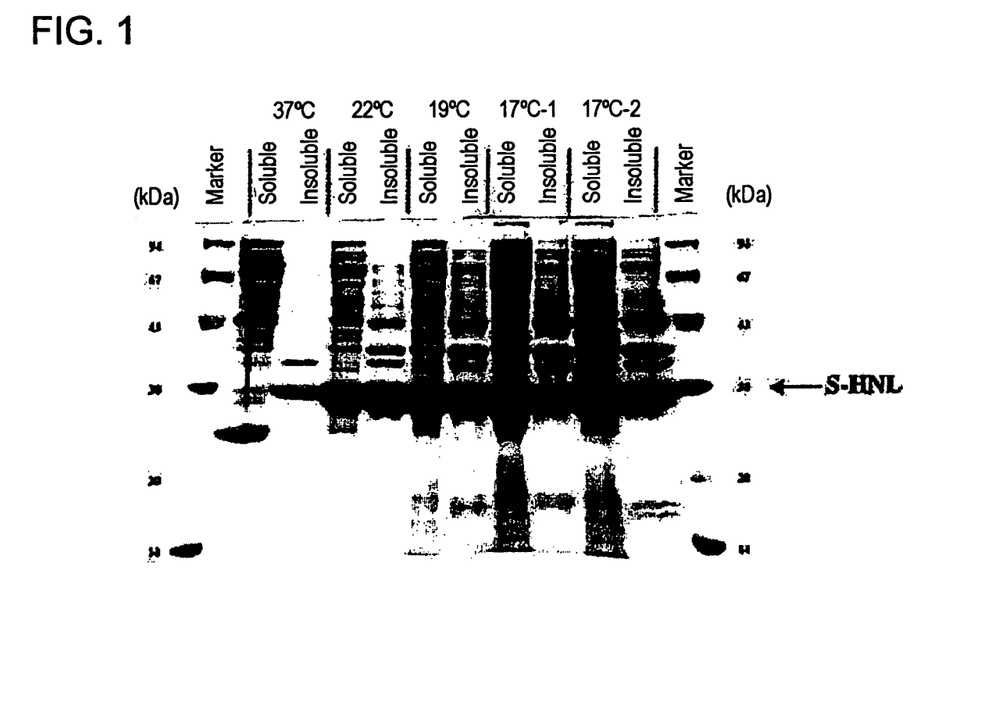
FIG. 1 is a diagram showing the results of the analysis performed on the soluble supernatant and the insoluble precipitate obtained in Example 2 to determine the expression of protein by using SDS-PAGE method.

The soluble supernatant and the insoluble precipitate were assayed for protein by the well-known method resorting to the SDS-polyacrylamide gel electrophoresis (SDS-PAGE). 20 μL per well was applied as diluted till the OD value reached a fixed level in the SDS-PAGE analysis. The results are shown in FIG. 1.

Example 3

For the purpose of determining what effect the cultivation temperature would bring on the dissolved oxygen concentration in the culture broth, the BL21/pET21a/Semba was cultured by the following method.

First, in a 500-mL Sakaguchi flask, 2 mL of the transformed *Escherichia coli* BL21/pET21a/Semba organized in Example 1 was inoculated to 100 mL of the nutritive culture medium described in Example 2 and precultured at a temperature of 37° C. at a shaking rate of 130 rpm for 12 hours. Subsequently, in a 2-L jar fermenter, 25 mL of the preculture broth was inoculated to 1200 mL of the nutritive culture medium described in Example 2, is 6propyl-β-D-thiogalactopyranoside (IPTG), a protein expression inducing agent, was added thereto till the final concentration thereof reached 1 mM, and they were subjected to production culture at a agitation rate of 680 rpm, an aeration rate of 1 vvm, and a temperature of 17° C. The cultivation time used herein was the time which elapsed till the culture reached the stationary state. During the course of the culture mentioned above, the culture broth was sampled at intervals of six hours. The cell pellet was collected by centrifugation of the culture broth and homogenized. Then the homogenate was divided into a soluble supernatant and an insoluble precipitate fraction.

Figure 2:
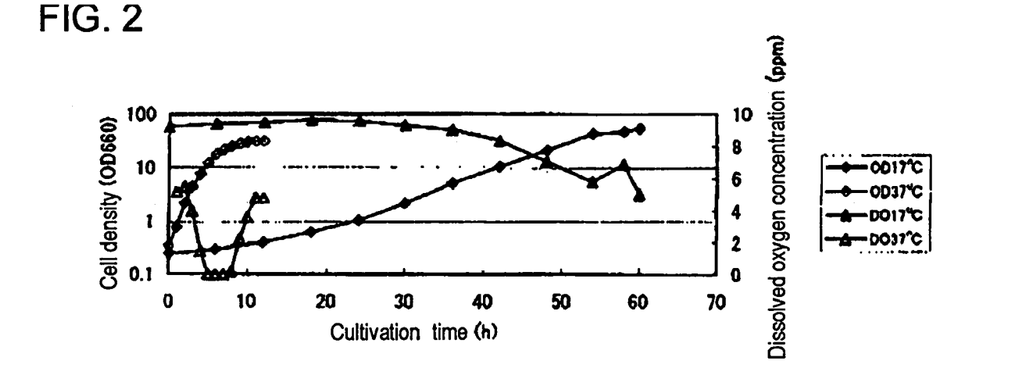
FIG. 2 is a diagram showing the relation between the cultivation temperature, and the cell density and the dissolved oxygen concentration in the jar fermenter culture obtained in consequence of the measurement of the cell density and the dissolved oxygen concentration in Example 3.

The samples of culture broth were obtained at intervals of six hours during the course of the culture mentioned above and cell density was measured. Dissolved oxygen concentration (DO) was measured by the use of a dissolved oxygen meter provided with an oxygen electrode (made by Marubishi BioEngineering K.K.), and it recorded every 6 hours during the culture. The results are shown in FIG. 2.

Comparative Example 3

The same gene recombinant *Escherichia coli* BL21/pET21a/Semba as used in Example 3 was cultured by following the procedure of Example 3while the cultivation temperature was changed to 37° C. Final cell density of the produced culture broth was measured. Dissolved oxygen concentration was also measured by the use of a dissolved oxygen meter provided with an oxygen electrode (made by Marubishi BioEngineering K.K.). The results are shown in FIG. 2.

Results:

As noted from Table 1, a difference in an insert brought a large difference in the final cell density and in the magnitude of SHNL activity. The activity was confirmed in two strains having an insert and the magnitude of specific activity showing the ability to produce the enzyme per cell unit was more than twice as high in the strain having a Semba gene as an insert than in the strain having an Ori gene as an insert. These data indicate that in the Semba gene, the alteration of a codon was effective in exalting the ability to produce a recombinant SHNL.

It is seen from Table 4 that the culture performed at a low temperature resulted in largely increasing the magnitude of activity and the magnitude of specific activity. When the culture was performed at 37° C., the magnitude of specific activity was only 0.17 U/mg-protein. By setting the cultivation temperature at 17° C., the specific activity increased to 29.08 U/mg-protein, a magnitude 170 times the magnitude obtained at 37° C. When the culture was performed at 37–27° C., the specific activity stopped increasing at a comparatively early stage and then began decreasing. When the culture was performed at a low temperature, the increase of the specific activity continued over a long time.

It is noted from FIG. 1 that a difference in temperature resulted in changing the ratio of the soluble fraction and the insoluble fraction of the produced SHNL. At 37° C., a band appeared in the soluble fraction of about 10%. At 22° C. and 19° C., the ratio of the soluble fraction and the insoluble fraction was nearly half and half. At 17° C., the ratio of the soluble fraction increased conspicuously. Further, by performing the culture at a low temperature, the total amount of SHNL to be produced was enabled to increase with a leap. These results indicate that, by performing the culture at a low temperature, it was made possible to repress the formation of an insoluble inclusion body and produce the active soluble SHNL protein in a large amount.

It is clear from FIG. 2 that the final cell concentration (OD value) was 54 at 17° C., a value nearly twice the OD value at 37° C. Further, the specific growth rate at 17° C. was about one eighth of that of the culture at 37° C. The dissolved oxygen concentration in the culture broth at 17° C. did not fall to 0 till the culture was completed, whereas it fell to 0 after the elapse of five hours following the start of the culture at 37° C. These results indicate that in the culture at a low temperature, the system was maintained in an aerobic environment, the energy source efficiency of cells was not lowered, and the SHNL was produced with high efficiency.

The entire disclosure of Japanese Patent Application No. 2002-365675 filed on Dec. 17, 2002 including specification, claims, drawings, and summary are incorporated herein by reference in its entirety.

What is claimed is:

1. A DNA molecule consisting of SEQ ID NO:2.
2. A recombinant vector containing the DNA molecule set forth in claim 1.
3. A recombinant vector according to claim 2, wherein the vector is a pET vector.
4. An *Escherichia coli* cell containing the recombinant vector set forth in claim 2.
5. An *Escherichia coli* cell containing the recombinant vector set forth in claim 3.
6. A method for the production of S-hydroxynitrile lyase, comprising the steps of culturing the *Escherichia coli* cell set forth in claim 4 at a temperature in the range of 10–35° C. and isolating said enzyme from the culture.
7. A method for the production of S-hydroxynitrile lyase, comprising the steps of culturing the *Escherichia coli* cell set forth in claim 5 at a temperature in the range of 10–35° C. and isolating said enzyme from the culture.

* * * * *